United States Patent
Springer et al.

(10) Patent No.: US 7,358,385 B2
(45) Date of Patent: Apr. 15, 2008

(54) BICYCLO[4.3.0]NONANE-3(4),7(8)-DICARBOXYLIC ACID AND A PROCESS FOR ITS PREPARATION

(75) Inventors: Helmut Springer, Dinslaken (DE); Paolo Bavaj, Frankfurt (DE)

(73) Assignee: Oxea Deutschland GmbH, Oberhausen (DE)

( * ) Notice: Subject to any disclaimer, the term of this patent is extended or adjusted under 35 U.S.C. 154(b) by 0 days.

(21) Appl. No.: 11/657,760

(22) Filed: Jan. 25, 2007

(65) Prior Publication Data

US 2007/0179314 A1 Aug. 2, 2007

(30) Foreign Application Priority Data

Jan. 31, 2006 (DE) .................... 10 2006 004 319

(51) Int. Cl.
*C07C 67/08* (2006.01)
(52) U.S. Cl. ......................................... 560/99
(58) Field of Classification Search .................. None
See application file for complete search history.

(56) References Cited

U.S. PATENT DOCUMENTS

| 3,271,365 A | | 9/1966 | Parham | |
|---|---|---|---|---|
| 4,262,147 A | * | 4/1981 | Garrou et al. | 568/817 |
| 5,041,675 A | * | 8/1991 | Lukas et al. | 564/446 |

OTHER PUBLICATIONS

Journal of the American Chemical Society (1958) 80, S. 5502-5 Cyclic Polyolefins Arthur Cope and William Keller.

* cited by examiner

*Primary Examiner*—Shaojia Anna Jiang
*Assistant Examiner*—M Louisa Lao
(74) *Attorney, Agent, or Firm*—Charles A. Muserlian

(57) ABSTRACT

The compound, bicyclo[4.3.0]nonane-3(4),7(8)-dicarboxylic acid and to a process for its preparation, wherein bicyclo[4.3.0]nona-3,7-diene is reacted with synthesis gas in an homogeneous organic phase in the presence of transition metal compounds of Group VIII of the Periodic Table containing complex-bound organophosphorus compounds, and of excess organophosphorus compound, at temperatures of 70 to 160° C. and pressures of 5 to 35 MPa, and the 3(4),7(8)-bisformylbicyclo[4.3.0]nonane thus obtained is oxidized, or is first hydrogenated to 3(4),7(8)-dihydroxymethylbicyclo[4.3.0]nonane and the diol thus obtained is reacted in an alkali melt.

16 Claims, No Drawings

BICYCLO[4.3.0]NONANE-3(4),7(8)-DICARBOXYLIC ACID AND A PROCESS FOR ITS PREPARATION

The present invention relates to bicyclo[4.3.0]nonane-3 (4),7(8)-dicarboxylic acid and to a process for its preparation from bicyclo[4.3.0]nona-3,7-diene.

STATE OF THE ART

Fused alicyclic unsaturated hydrocarbons with isolated double bonds in the rings are valuable starting materials which can be converted to compounds with important uses. The cyclic and fused hydrocarbon skeleton imparts particular properties. One example of this compound class is dicyclopentadiene (DCP), which is readily available by dimerizing cyclopentadiene and is also prepared on an industrial scale, and can be converted to compounds with important uses, to which the tricyclodecane skeleton imparts particular properties. The compounds which are derived from DCP and have a tricyclodecane structure are frequently also referred to in the literature as TCD derivatives (Chemiker-Zeitung, 98, 1974, pages 70 to 76).

Especially the hydroformylation of DCP affords TCD aldehydes of interest, such as 3(4),8(9)-bisformyltricyclo [$5.2.1.0^{2,6}$]decane, also known as TCD dialdehyde, which is processed further to give important intermediates. Owing to its thermal lability, which leads to losses in the course of distillative workup, TCD dialdehyde is usually not isolated in pure form but rather processed further as the crude product of the hydroformylation reaction.

The preparation of aldehydes by catalytic addition of carbon monoxide and hydrogen to olefinic double bonds is known. While this reaction used to be performed virtually exclusively with cobalt as the catalyst, modern processes work with metallic rhodium or with rhodium compounds as catalysts, which are used alone or with complexing ligaments, for example organophosphines or esters of phosphorus acid. According to the unanimous opinion in the technical field, catalysts effective under the reaction conditions are hydrido carbonyl compounds of rhodium which can be reproduced by the formula $H[Rh(CO)_{4-x}L_x]$ where L is a ligand and x is 0 or an integer from 1 to 3.

A special case is the hydroformylation of dienes. While almost exclusively monoaldehydes are obtained under the customary conditions of the oxo process in the hydroformylation of conjugated dienes, it is possible to obtain not only the mono- but also the disubstitution products from dicyclopentadiene (DCP) with its isolated double bonds. Owing to the great significance of the hydroformylation products of DCP, there are also numerous studies in the technical literature which address both the hydroformylation reaction of DCP and the subsequent workup of the crude product. For instance, DE 38 22 038 A1 and GB 1 170 226 consider the hydroformylation of DCP in the presence of rhodium in an organic solvent at elevated pressure and elevated temperature. A comprehensive review of the hydroformylation of dicyclopentadiene can be found in the Chemiker-Zeitung 98, 1974, 70-76, where reference is likewise made to the thermal lability of the TCD aldehydes, which leads to high product losses in the distillative workup of the crude hydroformylation mixture. Therefore, TCD dialdehydes are usually not isolated in pure form but processed further in their mixtures with the by-products of the oxo process. However, indications of extractive workup processes without thermal stress can also be found in the prior art, for example in EP-1 065 194 A1 or U.S. Pat. No. 5,138,101 A. In these processes, the organic crude mixture is extracted with a polar organic solvent, for example with a polyhydric alcohol or with a methanol/water mixture, which transfers the TCD dialdehydes to the polar alcoholic phase, and the hydroformylation catalyst remains in the hydrocarbon phase.

TCD dialdehydes are processed further to important intermediates. For instance, the oxidation of TCD dialdehyde leads to tricyclo[$5.2.1.0^{2,6}$]-decane-3(4),8(9)-dicarboxylic acid, also known as TCD acid DS, which has great economic significance as a valuable intermediate for the chemical industry (J. Prakt. Chem. 14, (1961), 71; Chemiker-Zeitung 98, 1974, pages 70-76).

A further route to the dicarboxylic acid is opened up via the alkali melt of the TCD alcohol DM {3(4),8(9)-dihydroxymethyltricyclo[$5.2.1.0^{2,6}$]-decane} obtained by hydrogenating TCD dialdehyde. The alkali melt is effected by reacting the alcohol with molten alkali metal hydroxide at elevated temperature and elevated pressure, and leads to the alkali metal salts of the acid with evolution of hydrogen (U.S. Pat. Nos. 2,881,208 A 2,875,244 A, FR 1,155,677 A).

The divalent TCD acid DS is of high industrial interest for different applications in various ways, for example as an acid component in coating and synthetic resin formulations, for plasticizers and in lubricant oils (U.S. Pat. Nos. 2,875, 244 A, 2,881,208 A).

OBJECTS OF THE INVENTION

It is an object of the invention to provide the chemical compound, bicyclo[4.3.0.]nonane-3(4),7(8)-dicarboxylic acid.

It is another object of the invention to provide a novel, inexpensive process to provide dicarboxylic acid having a cyclic hydrocarbon skeleton from fused, alicyclic hydrocarbons in high purity.

These and other objects and advantages of the invention will become obvious from the following detailed description.

THE INVENTION

The process of the invention comprises preparing bicyclo [4.3.0]-nonane-3(4),7(8)-dicarboxylic acid by hydroformylating bicyclo[4.3.0]nona-3,7-diene with subsequent oxidation. It comprises reacting bicyclo[4.3.0]nona-3,7-diene with synthesis gas in an homogeneous organic phase in the presence of transition metal compounds of Group VIII of the Periodic Table containing complex-bound organophosphorus compounds, and of excess organophosphorus compound, at temperatures of 70 to 160° C. and pressures of 5 to 35 MPa, and then oxidizing the 3(4),7(8)-bisformylbicyclo[4.3.0]nonane thus obtained to form bicyclo[4.3.0] nonane-3(4),7(8)-dicarboxylic acid.

The invention further consists in a process for preparing bicyclo[4.3.0]-nonane-3(4),7(8)-dicarboxylic acid by hydroformylating bicyclo[4.3.0]nona-3,7-diene with subsequent hydrogenation and then reaction in an alkali melt. It comprises reacting bicyclo[4.3.0]nona-3,7-diene with synthesis gas in homogeneous organic phase in the presence of transition metal compounds of Group VIII of the Periodic Table containing complex-bound organophosphorus compounds, and of excess organophosphorus compound, at temperatures of 70 to 160° C. and pressures of 5 to 35 MPa, hydrogenating the 3(4),7(8)-bisformylbicyclo[4.3.0]nonane thus obtained to obtain 3(4),7(8)-dihydroxymethyl-bicyclo [4.3.0.]nonane, reacting the 3(4),7(8)-dihydroxymethylbicyclo[4.3.0.]nonane thus obtained in an alkali melt at elevated temperature and elevated pressure, and then releasing bicyclo[4.3.1.]nonane-3(4),7(8)-dicarboxylic acid.

The inventive compound derives from bicyclo[4.3.0]nona-3,7-diene, which is prepared industrially by Diels-Alder reaction of butadiene with cyclopentadiene and which is therefore available in inexpensive amounts.

The numbering of the carbon atoms bonded in the unsaturated, bicyclic hydrocarbon is according to the following sequence:

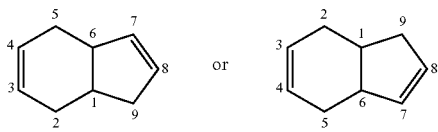

the two structural formulae being identical.

The inventive compound, bicyclo[4.3.0]nonane-3(4),7(8)-dicarboxylic acid, is a mixture of different isomers of bicyclo[4.3.0]nonanedicarboxylic acid in which the carboxyl groups in the six-membered ring can be bonded once at the 3- or at the 4-position, and the carboxyl group in the five-membered ring once at the 7- or at the 8-position.

In analogy to the notation customary for the TCD derivatives according to Chemiker-Zeitung, 98, 1974 pages 70 to 76, the inventive compound, bicyclo[4.3.0.]nonane-3(4),7(8)-dicarboxylic acid, can be described in terms of formula as follows:

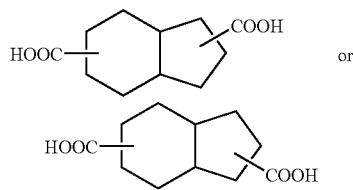

the two structural formulae being identical.

The starting material, bicyclo[4.3.0]nona-3,7-diene can be supplied to the hydroformylation as such or in solution. Suitable solvents are those in which starting material, reaction product and catalyst are soluble and which behave inertly under the reaction conditions, for example water-insoluble ketones, dialkyl ethers, aliphatic nitriles, aromatic hydrocarbons such as benzene, toluene, isomeric xylenes or mesitylene, and saturated cycloaliphatic hydrocarbons such as cyclopentane or cyclohexane, or saturated aliphatic hydrocarbons such as n-hexane, n-heptane or n-octane. The proportion of the solvent in the reaction medium can be varied over a wide range and is typically from 10 to 80% by weight, preferably from 20 to 50% by weight, based on the reaction mixture.

The hydroformylation stage is performed in a homogeneous reaction system. The term homogeneous reaction system means a homogeneous solution composed essentially of solvent, if added in the reaction stage, catalyst, excess organophosphorus compound, unconverted starting compound and hydroformylation product.

The catalysts used are transition metal compounds of Group VIII of the Periodic Table which contain complex-bound organophosphorus compounds. Preference is given to using complexes of cobalt, rhodium, iridium, nickel, iron, platinum, palladium or ruthenium, and especially of cobalt, rhodium and iridium. Particular preference is given to the use of rhodium complexes which contain organic phosphorus (III) compounds as ligands. Such complexes and their preparation are known (for example from U.S. Pat. Nos. 3,527,809 A, 4,148,830 A, 4,247,486 A and 4,283,562 A). They may be used as homogeneous complexes or as a mixture of different complexes. The rhodium concentration in the reaction medium extends over a range of from 5 to 1000 ppm by weight and is preferably from 10 to 700 ppm by weight. In particular, rhodium is employed in concentrations of from 20 to 500 ppm by weight, based in each case on the homogeneous reaction mixture.

The hydroformylation is performed in the presence of a catalyst system composed of rhodium-organophosphorus complex and free, i.e. excess, organophosphorus ligand which does not enter into a complex with rhodium. The free organophosphorus ligand may be the same as in the rhodium complex, but it is also possible to use different ligands. The free ligand may be a homogeneous compound or consist of a mixture of different organophosphorus compounds. Examples of rhodium-organophosphorus complexes which may find use as catalysts are described in U.S. Pat. No. 3,527,809 A.

The preferred ligands in the rhodium complex catalysts include, for example, triarylphosphines such as triphenylphosphine, trialkylphosphines such as tri(n-octyl) phosphine, trilaurylphosphine, tri(cyclohexyl)phosphine, alkylarylphosphines, alkyl phosphites, aryl phosphites, alkyl diphosphites and aryl diphosphites. For instance, it is likewise possible to use rhodium complexes which contain aryl phosphites of the formula $P(OR^1)(OR^2)(OR^3)$ in complex-bound form, where at least one of the $R^1$, $R^2$ or $R^3$ groups is an ortho-substituted phenyl ring.

Suitable complex ligands have been found to be tris(2-tert-butylphenyl) phosphite or tris(2-tert-butyl-4-methylphenyl) phosphite. The rhodium-catalyzed hydroformylation of olefins with phosphite-modified complexes is known from EP 0 054 986 A1. Owing to its easy availability, triphenylphosphine is employed particularly frequently.

Typically, the molar ratio of rhodium to phosphorus in the homogeneous reaction mixture is from 1:5 to 1:200, but the molar proportion of the phosphorus in the form of organic phosphorus compounds may also be higher. Preference is given to using rhodium and organically bound phosphorous in molar ratios of from 1:10 to 1:100.

When a transition metal of Group VIII of the Periodic Table other than rhodium is used in the hydroformylation stage, the concentration of transition metal and the molar ratio of transition metal to phosphorus is within the ranges which are also selected for rhodium. The optimal values in each case can be determined by simple routine tests depending on the transition metal used in each case.

The conditions under which the hydroformylation proceeds can vary within wide limits and can be adjusted to the individual circumstances. They depend upon factors including the starting material, the catalyst system used and the desired conversion. Typically, the hydroformylation of bicyclo[4.3.0]nona-3,7-diene is performed at temperatures of 70 to 160° C. Preference is given to maintaining temperatures of 80 to 150° C. and in particular, 90 to 140° C. The total pressure extends over a range of from 5 to 35 MPa, preferably from 10 to 30 MPa and in particular, 20 to 30 MPa. The molar ratio of hydrogen to carbon monoxide varies typically between 1:10 and 10:1; mixtures which contain hydrogen and carbon monoxide in a molar ratio of from 3:1 to 1:3, especially about 1:1, are particularly suitable.

The catalyst is typically formed from the transition metal or transition metal compound, organophosphorus compound and synthesis gas under the conditions of the hydroformylation reaction in the reaction mixture. However, it is also possible first to preform the catalyst and then to feed it to the actual hydroformylation stage. The conditions of the preformation correspond generally to the hydroformylation conditions.

For the preparation of the hydroformylation catalyst, the transition metal of Group VIII of the Periodic Table, especially rhodium, is used either in metallic form or as a compound. In metallic form, the transition metal is used either in the form of fine particles or in a thin layer on a support, such as activated carbon, calcium carbonate, aluminium silicate, alumina. Suitable transition metal compounds are salts of aliphatic mono- and polycarboxylic acids such as transition metal 2-ethylhexanoates, acetates, oxalates, propionates or malonates. In addition, it is possible to use salts of inorganic hydrogen and oxygen acids such as nitrates or sulfates, the various transition metal oxides or transition metal carbonyl compounds such as $Rh_3(CO)_{12}$, $Rh_6(CO)_{16}$, $CO_2(CO)_8$, $CO_4(CO)_{16}$, $Fe(CO)_5$, $Fe_2(CO)_9$, $Ir_2(CO)_8$, $Ir_4(CO)_{12}$ or transition metal complexes, for example cyclopentadienylrhodium compounds, rhodium acetylacetonate, cyclopentadienylcobalt(cyclooctodiene-1, 5), $Fe(CO)_3$(cyclooctadiene-1,5), [RhCl(cyclooctadiene-1, 5]$_2$ or $PtCl_2$(cyclooctadiene-1,5). Transition metal-halogen compounds are less useful owing to their corrosive behavior of the halide ions.

Preference is given to transition metal oxides and, in particular, transition metal acetates and 2-ethylhexanoates. Particular suitable compounds have been found to be rhodium oxide, rhodium acetate, rhodium 2-ethyl-hexanoate, cobalt oxide, cobalt acetate and cobalt 2-ethylhexanoate.

The hydroformylation stage may be performed either batchwise or continuously. In the process according to the invention, the starting olefin bicyclo[4.3.0]nona-3,7-diene is converted virtually completely, and a crude hydroformylation product having a content of the desired bisformyl product which is usually above 75% by weight based on the crude hydroformylation product is obtained.

The reaction product of the hydroformylation stage is usually processed further without purification and without catalyst removal; appropriately, however, a distillative purification of the dialdehyde follows before further processing.

In one embodiment of the process according to the invention, the appropriately purified aldehydes are reacted with oxygen or oxygen-containing gases or in the presence of a customary oxidizing agent, for example, hydrogen peroxide, alkali metal hypochlorites or potassium permanganate. Preference is given to the use of oxygen or oxygen-containing gases, both in the absence and in the presence of oxidation catalysts.

Further constituents of such gas mixtures are inert gases, for example nitrogen, noble gases and carbon dioxide. The proportion of the inert constituents of the oxygen-containing gas mixture is up to 90% by volume, in particular from 30 to 80% by volume. The preferred oxidizing agents are oxygen or air.

Useful catalysts for the oxidation step are predominantly salts of transition metals, especially salts of cobalt and of manganese, and also of chromium, iron, copper, nickel, silver and vanadium, as known, for example, from DE 100 10 771 C1. Addition of alkali metal salts of weak acids may also have an advantageous effect on the selectivity for the desired dicarboxylic acid.

The aldehydes are used dissolved in a solvent which is inert under the reaction conditions. The addition of a solvent is required, since the bicyclo[4.3.0.]nonane-3(4),7(8)-dicarboxylic acid formed in the oxidation is solid at room temperature. Examples of suitable solvents are ketones such as acetone, esters, e.g. ethyl acetate, hydrocarbons, e.g. toluene, and nitrohydrocarbons such as nitrobenzene. The concentration of the aldehyde is limited by its solubility and by the solubility of the dicarboxylic acid formed in the solvent.

The oxidation step may be performed batchwise or continuously and recycling of unconverted reaction participants is possible in both cases.

In a proven embodiment, 3(4),7(8)-bisformylbicyclo [4.3.0.]nonane is initially charged together with a solvent, such as toluene, in a suitable reactor, for example in a tubular reactor provided with a flow tray which optionally also contains random packings, and the oxygen or the oxygen-containing gas mixture is passed from the bottom through the aldehyde: The reactants are reacted within a temperature range of 20 to 80° C., preferably 40 to 80° C., at standard pressure. However, the use of elevated pressure is not ruled out. Typically a range of from standard pressure to 1.0 MPa is employed, preferably from standard pressure to 0.8 MPa.

According to a further embodiment, the reactor used is a trickle tower which contains random packings. The aldehyde is allowed to trickle down through the random packing, and oxygen or an oxygen-containing gas mixture is simultaneously passed into the tower in concurrent or counter-current flow.

After removal of the solvent, the desired bicyclo[4.3.0] nonane-3(4),7(8)-dicarboxylic acid is obtained as a solid which can be purified further by suitable measures, for example by resalting and recrystallization.

In a further embodiment of the process of the invention, 3(4),7(8)-bisformylbicyclo[4.3.0]nonane is first hydrogenated to 3(4),7(8)-dihydroxymethylbicyclo[4.3.0]nonane, and then reacted in an alkali melt at elevated temperature and elevated pressure.

The hydrogenation of the crude or optionally purified 3(4),7(8)-bisformylbicyclo[4.3.0]nonane to give 3(4),7(8)-dihydroxymethylbicyclo[4.3.0]nonane is effected under customary reaction conditions in the presence of conventional hydrogenation catalysts. In general, the hydrogenation temperature is 70 to 170° C. and the pressure employed is 1 to 30 MPa. Suitable hydrogenation catalysts are particularly nickel catalysts.

The catalytically active metal can be applied on a support, generally in an amount of about 5 to about 70% by weight, preferably about 10 to 65% by weight and in particular, about 20 to about 60% by weight, based in each case on the total weight of the catalyst. Suitable catalyst supports are all conventional support materials, for example aluminum oxide, aluminum oxide hydrates in their various manifestations, silicon dioxide, polysilicic acids (silica gels) including kieselguhr, silica xerogels, magnesium oxide, zinc oxide, zirconium oxide and activated carbon.

In addition to the main components of nickel and support material, the catalysts may also comprise additives in minor amounts, which serve, for example, to improve their hydrogenation activity and/or their lifetime and/or their selectivity. Such additives are known and include, for example, the oxides of sodium, potassium, magnesium, calcium, barium, zinc, aluminum. zirconium and chromium. They are added to the catalyst generally in a total proportion of from 0.1 to 50 parts by weight based on 100 parts by weight of nickel.

However, it is also possible to use unsupported catalysts such as Raney nickel or Raney cobalt in the hydrogenation process. The hydrogenation stage is performed batchwise or continuously in the liquid phase with suspended catalysts or in the liquid or gaseous phase with fixed bed catalysts. The continuous procedure is preferred.

The hydrogenation is effected preferably with pure hydrogen. However, it is also possible to use mixtures which comprise free hydrogen and additionally constituents which are inert under the hydrogenation conditions. In any case, it should be ensured that the hydrogenation gas is free of catalyst poisons such as sulfur compounds or carbon monoxide in harmful amounts.

The diol thus obtained is then appropriately purified by distillation and then reacted in an alkali melt at elevated temperature, generally from 200 to 350° C., and at elevated pressure, generally from 0.5 to 5 MPa. To prepare the alkali melt, alkali metal hydroxides such as sodium hydroxide or potassium hydroxide, and mixtures thereof are used. Typically, the weight ratio of diol to alkali metal hydroxide is from 1:2.1 to 1:2.6, preferably 1:2.1 to 1:2.3. During the reaction, there is release of hydrogen, so that the reaction is preferably performed in a closed pressure vessel. It is appropriate to work in the absence of solvents, even though the reaction can also be performed in the presence of high-boiling inert solvents.

Once the reaction has ended, the reaction mixture is admixed with water and neutral by-products can be extracted with an organic solvent, for example toluene. The water phase is then acidified and the released dicarboxylic acid in the organic phase obtained is removed. Here too, the use of a suitable organic solvent is possible. If necessary, the dicarboxylic acid thus prepared can be freed from the organic solvent used under reduced pressure, or be purified further by recrystallization.

The process according to the invention permits a simple and inexpensive route to bicyclo[4.3.0]nonane-3(4),7(8)-dicarboxylic acid in high yield and in high purity. The dicarboxylic acid prepared by the process of the invention can be used in an excellent manner for different applications, for example as a constituent in coating and synthetic resin formulations, for plasticizers and in lubricant oils.

In the following examples, there are described several preferred embodiments of the process of the invention. However, it should be understood that the invention is not intended to be limited to the specific embodiments.

EXAMPLE 1

Preparation of bicyclo[4.3.0]nonane-3(4),7(8)-dicarboxylic acid

1. Preparation of 3(4),7(8)-bisformylbicyclo[4.3.0]nonane

A steel autoclave with a magnetic stirrer was initially charged with 1,000 g of bicyclo[4.3.0]nona-3,7-diene in technical quality and 1,000 g of toluene. After adding 12.75 g of triphenylphosphine and 50 mg of rhodium in the form of a toluenic solution of rhodium 2-ethylhexanoate having a content of 7,062 mg of Rh/kg, the mixture was heated to 130° C. and treated with synthesis gas under a pressure of 26 MPa. After a reaction time of 8 hours, the hydroformylation reaction was ended.

The organic phase was analyzed by gas chromatography.

| GC analysis (area percent without toluene) | |
|---|---|
| components in first runnings | 0.2 |
| bicyclo[4.3.0]nona-3,7-diene range | 0.1 |
| components | 4.6 |
| 3(4),7(8)-bisformylbicyclo[4.3.0]nonane | 89.1 |
| triphenylphosphine/triphenylphosphine oxide | 1.2 |
| high boilers | 4.8 |

EXAMPLE 2

Preparation of bicyclo[4.3.0]nonane-3(4),7(8)-dicarboxylic acid

Alkali Melt of 3(4),7(8)-dihydroxymethylbicyclo[4.3.0]nonane

Preparation of 3(4),7(8)-dihydroxymethylbicylco[4.3.0]nonane

The crude 3(4),7(8)-bisformylbicyclo[4.3.0]nonane obtained after the hydroformylation was freed largely of the toluene by distillation on a thin-film evaporator (jacket temperature 140° C., pressure 100 hPa). A residue was obtained which, by gas chromatography analysis, also contained 9.5% other components in addition to 6.7% toluene and 83.8% of 3(4),7(8)-bisformylbicyclo[4.3.0]nonane.

Subsequently, 700 g of the residue diluted with 300 g of isobutanol, and 42 g of Ni 52/35 catalyst from Johnson Matthey Plc, were initially charged in a 3 liter autoclave. The reaction mixture was heated to 130° C. and reacted at a pressure of 10.0 MPa and a reaction time of 8 hours. After the reaction had ended, the reaction mixture was cooled, decompressed and filtered from the catalyst to obtain the reaction product which was analyzed by gas chromatography.

| GC analysis (in area percent) | |
|---|---|
| components in first runnings | 1.3% |
| isobutanol/toluene/methylcyclohexane | 29.2% |
| 3(4),7(8)-dihydroxymethylbicyclo[4.3.0]nonane | 62.8% |
| others | 6.7% |

For workup, the crude hydrogenation product was distilled using a Claisen distillation system starting from 825.3 g, 459.3 g of main fraction in a boiling range of 178-179° C. were obtained at a pressure of 1 hPa with the following composition:

| GC analysis (in area percent) | |
|---|---|
| components in first runnings | 0.1% |
| 3(4),7(8)-dihydroxymethylbicyclo[4.3.0]nonane | 97.3% |
| others | 2.6% |

Alkali melt of 3(4),7(8)-dihydroxymethylbicyclo[4.3.0]nonane

The 3(4),7(8)-dihydroxymethylbicyclo[4.3.0]nonane obtained after the hydrogenation of 3(4),7(8)-bisformylbicyclo[4.3.0]nonane and subsequent distillation was introduced into the alkali melt. 184.3 g of the diol were initially charged together with 12.0 g of acetic acid in a 1 liter autoclave and admixed with 57.6 g of NaOH (solid, pure) and 62.6 g of KOH (solid, 85%). The mixture was heated to 250° C. with stirring, in the course of which the pressure was regulated to 2 MPa. After 2 hours at 250° C., the temperature was increased to 280° C.; the pressure remained at 2 MPa. After a reaction time of 2 hours at 280° C., the mixture was cooled, while water was pumped in an amount of 300 g at about 160° C. The resulting solution was admixed with 185.0 g of toluene and acidified by adding 1,813 g of 20% aqueous sulfuric acid. The organic phase was subsequently extracted five times with 300.0 g of water. After the solvent had been distilled off, the desired dicarboxylic acid was obtained as a solid in the distillation residue. The weight of bicyclo[4.3.0]nonane-3(4),7(8)-dicarboxylic acid was 197.1 g at a purity of 99.07%.

Elemental Analysis $C_{11}H_{16}O_4$ (212.2) Calc. C 62.3%, H 7.6%, O 30.2% Found. C 63.3%, H 7.2%, O 27.7%

NMR Data $^1$H NMR (500 MHz, DMSO-$d_6$, ppm): 1.06-2.88 (m, 14 H, CH and $CH_2$), 11.95 (s, 2H, COOH)

$^{13}$C NMR (125 MHz, DMSO-$d_6$, ppm): 21.02-49.24 (CH and $CH_2$), 174.64-177.97 (COOH)

IR Data (Diamond ATR-IR Spectroscopy)

$\nu$ ($cm^{-1}$) 3000 (m, br), 2933 (m), 2865 (m), 1691 (s), 926 (m)

Oxidation of
3(4),7(8)-bisformylbicyclo[4.3.0]nonane

The liquid phase oxidation of 3(4),7(8)-bisformylbicyclo[4.3.0]nonane to bicyclo[4.3.0]nonane-3(4),7(8)-dicarboxylic acid was performed without catalyst addition in a glass bubble column reactor having an internal diameter of 38 mm and length of 150 cm. Depending on the reaction behavior, the reactor was cooled or heated on the jacket side by a water circuit connected to a heat exchanger, and the internal temperature was thus kept constant. The oxygen was supplied from the bottom through a glass filter plate connected to the bubble column reactor with a maximum pore width of 16-40 μm.

467.8 g of dialdehyde with a content of 15.6% toluene, 71.4% 3(4),7(8)-bisformylbicyclo[4.3.0]nonane and 13.0% other components, which were obtained after solvent removal on a thin-film evaporator according to example 2.1.1, were introduced into the oxidation. The product was mixed with 322.0 g of toluene and with 42.5 g of a solution consisting of potassium 2-ethylhexanoate and 2-ethylhexanoic acid with a potassium content of 5.7%. After a reaction time of 6 hours at a constant 60° C., a crude acid of the following composition was obtained:

| GC analysis (area percent without toluene and 2-ethylhexanoic acid): | |
|---|---|
| 3(4),7(8)-bisformyltricyclo[4.3.0]nonane | 4.7% |
| bicyclo[4.3.0]nonane-3(4),7(8)-dicarboxylic acid | 75.5% |
| others | 19.8% |

The process of the invention opens up an elegant preparative route for bicyclo[4.3.0]nonane-3(4),7(8)-dicarboxylic acid in high yields. The novel compound bicyclo[4.3.0]nonane-3(4),7(8)-dicarboxylic acid has an alicyclic ring structure with fused rings, which is outstandingly suitable as a constituent for coating and synthetic resin formulations.

Various modifications of the process of the invention may be made without departing from the spirit or scope thereof and it is to be understood that the invention is intended to be limited only as defined in the appended claims.

What is claimed is:

1. A process for preparing bicyclo[4.3.0]nonane-3(4),7(8)-dicarboxylic acid by hydroformylating bicyclo[4.3.0]nona-3,7-diene with subsequent oxidation, which comprises reacting bicyclo[4.3.0]nona-3,7-diene with synthesis gas in an homogeneous organic phase in the presence of transition metal compounds of Group VIII of the Periodic Table containing complex-bound organophosphorus compounds, and of excess organophosphorus compound, at temperatures of 70 to 160° C. and pressures of 5 to 35 MPa, and then oxidizing the resulting 3(4),7(8)-bisformylbicyclo[4.3.0]nonane to obtain bicyclo[4.3.0]nonane-3(4),7(8)-dicarboxylic acid.

2. A process for preparing bicyclo[4.3.0]nonane-3(4),7(8)-dicarboxylic acid by hydroformylating bicyclo[4.3.0]nona-3,7-diene with subsequent hydrogenation and subsequent reaction in an alkali melt, which comprises reacting bicyclo[4.3.0]nona-3,7-diene with synthesis gas in an homogeneous organic phase in the presence of transition metal compounds of Group VIII of the Periodic Table containing complex-bound organophosphorus compounds, and of excess organophosphorus compound, at temperatures of 70 to 160° C. and pressures of 5 to 35 MPa, hydrogenating the 3(4),7(8)-bisformylbicyclo[4.3.0]nonane thus obtained to obtain 3(4),7(8)-dihydroxymethylbicyclo[4.3.0]nonane, reacting the 3(4),7(8)-dihydroxymethylbicyclo[4.3.0]nonane thus obtained in an alkali melt at elevated pressure, and then releasing bicyclo[4.3.0]nonane-3(4),7(8)-dicarboxylic acid.

3. The process of claim 1, wherein the organophosphorus compounds used are organic phosphorus(III) compounds selected from the group consisting of triarylphosphines, alkylarylphosphines, alkyl phosphites, aryl phosphites, alkyl diphosphites and aryl diphosphites.

4. The process of claim 3, wherein the triarylphosphine used is triphenylphosphine and the aryl phosphite used is tris(2-tert-butylphenyl) phosphite or tris(2-tert-butyl-4-methylphenyl) phosphite.

5. The process of claim 1, wherein the transition metal compounds of Group VIII of the Periodic Table used are selected from the group consisting of compounds of rhodium, cobalt, iridium, nickel, palladium, platinum, iron and ruthenium.

6. The process of claim 1, wherein the transition metal compounds of Group VIII of the Periodic Table used are compounds of rhodium.

7. The process of claim 1, wherein rhodium is used in a concentration of 5 to 1,000 ppm by weight based on the homogeneous reaction mixture.

8. The process of claim 7, wherein rhodium is used in a concentration of 10 to 700 ppm by weight, based on the homogeneous reaction mixture.

9. The process of claim 1, wherein the molar ratio of rhodium to phosphorus is 1:5 to 1.200.

10. The process of claim 9, wherein the molar ratio of rhodium to phosphorus is 1:10 to 1:100.

11. The process of claim 1, wherein the hydroformylation is performed at temperatures of 80 to 150° C., and at pressures of 10 to 30 MPa.

12. The process of claim 2, wherein the hydrogenation is performed in the presence of nickel catalysts at temperatures of 70 to 170° C. and at pressures of 1 to 30 MPa.

13. The process of claim 2, wherein 3(4),7(8)-dihydroxymethylbicyclo[4.3.0]nonane is reacted in an alkali melt at temperatures of 200 to 350° C. and at pressures of 0.5 to 5 MPa.

14. The process of claim 1, wherein the oxidation of 3(4),7(8)-bisformylbicyclo[4.3.0]nonane is performed at temperatures of 20 to 80° C. and at pressures of standard pressure to 1.0 MPa.

15. The process of claim 14, wherein the oxidizing agents used are oxygen or air.

16. The bicyclo[4.3.0]nonane-3(4),7(8)-dicarboxylic acid.

* * * * *